United States Patent [19]

Schirmann et al.

[11] 3,972,878
[45] Aug. 3, 1976

[54] METHOD FOR PREPARING AZINES AND HYDRAZONES

[75] Inventors: Jean-Pierre Schirmann, Brignais; Jean Combroux, Sainte-foy-les-Lyon; Serge Yvon Delavarenne, Francheville-le-Haut, all of France

[73] Assignee: Produits Chimiques Ugine Kuhlmann, Paris, France

[22] Filed: Feb. 7, 1975

[21] Appl. No.: 548,159

[30] Foreign Application Priority Data

Feb. 8, 1974  France .............................. 74.4247

[52] U.S. Cl. ..................... 260/240 G; 260/295 R; 260/295 AM; 260/296 R; 260/345.1; 260/346.1 R; 260/345.9; 260/465 E; 260/465.4; 260/465.5 R; 260/333; 260/345.7; 260/468 J; 260/347.3; 260/347.7; 260/471 R; 260/482 R; 260/514 J; 260/518 R; 260/518 A; 260/519; 260/534 R; 260/534 M; 260/558 A; 260/558 D; 260/559 A; 260/561 A; 260/566 B

[51] Int. Cl.² ...................................... C07C 109/00

[58] Field of Search..... 260/566 B, 295 R, 295 AM, 260/345.1, 345.9, 465 E, 465.4, 465.5 R, 468 J, 471 R, 482 R, 514 J, 518 R, 518 A, 519, 534 R, 534 M, 558 A, 558 D, 559 A, 561 A

[56] References Cited

OTHER PUBLICATIONS

Schirmann et al., *Tetrahedron Letters*, No. 7 pp. 635–636 (1972).
Mathais et al., *Tetrahedron Letters*, No. 6 pp. 529–530 (1972).

*Primary Examiner*—Gerald A. Schwartz
*Attorney, Agent, or Firm*—Pennie & Edmonds

[57] ABSTRACT

Ammonia and aldehydes or ketones are selectively oxidized by hydrogen peroxide to the corresponding azines when they are reacted in the presence of both (a) an amide of a carboxylic acid having a pK greater than about 4.3 and (b) a co-catalyst having the general formula H—X—Y=Z, wherein H is hydrogen, X and Z are each an atom of oxygen or nitrogen and Y is an atom of carbon, nitrogen, arsenic, antimony, phosphorus, sulfur, selenium or tellurium; the atoms of X, Y, and Z carrying other substituents necessary to obey the rules of valence. Preferred co-catalysts include di(alkali metal) hydrogen phosphates, lower dialkyl phosphate esters, bicarbonates and p-toluene sulfonic acid. When 1° or 2° amines are also present, hydrazones are also formed along with the azines. Uses of the resultant products include their hydrolysis to hydrazines with recycling of aldehyde or ketone.

21 Claims, No Drawings

METHOD FOR PREPARING AZINES AND HYDRAZONES

BACKGROUND OF THE INVENTION

The present invention provides a new catalytic procedure for preparing azines from ketones or aldehydes in the presence of ammonia and hydrogen peroxide.

It is known that aldehydes react with ammonia in a complex manner to form various products of addition, condensation or polymerization. (See S. Patai, *The Chemistry of the Carbon-Nitrogen Bond*, Interscience, London 1970 page 67). It is known also that aldehydes are capable of reacting with hydrogen peroxide to form unstable peroxide products and that aldehydes can react together with both hydrogen peroxide and ammonia to give rise to peroxide products. (See *J. Chem Soc.* 1969, C, page 2678).

It is likewise known that ammonia, hydrogen peroxide and a ketone can react together to produce aminoperoxides. (See, for example, *J. Chem. Soc.*, 1969, C, page 2663) and that these reactants in the presence of tungstic acid or molybdic acid catalyst, can produce an oxime. (See, for example, *J. Gen. Chem. (U.S.S.R.)* 1960, 30, page 1635).

It is known, furthermore, that primary and secondary amines are easily oxidized by various compounds into oxygenated products such as hydroxylamines, nitro or nitroso derivatives, oximes, azoxy compounds, amides and other related compounds depending on the particular structure of the reactants and the reaction conditions. For example, the oxidation of primary aliphatic amines into nitroalkanes by means of peracetic acid has been described in *J. Am. chem. Soc.* 79 5528 (1957). Similar reactions using other percarboxylic acids are described in *The Chemistry of the Nitro and Nitroso Groups* Part I, edited by H. Feuer, page 309 (Interscience, N.Y., 1969).

The primary aromatic amines have been oxidized into nitroso, nitro or corresponding azoxy derivatives by pure percarboxylic acids or by a mixture of acetic acid and hydrogen peroxide in 30% aqueous solution (*J. Am. Chem. Soc.* 82 3454 (1960)).

Aniline also has been oxidized to azoxybenzene by hydrogen peroxide in the presence of acetonitrile. (*J. Org. Chem.* 26 659 (1961)).

Now, earlier applications for patent, commonly assigned with the instant application, have described several new procedures for synthesizing azines (I) by oxidizing ammonia in the presence of a ketone or aldehyde carbonyl compound (IV) with various peroxide reagents according to the general scheme:

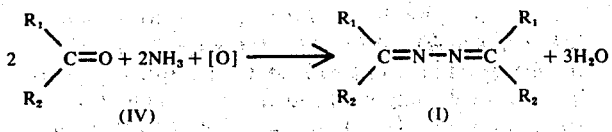

wherein $R_1$ and $R_2$ are alkyl or aryl groups.

In addition to the patent disclosures enumerated below, see also Tellier, Mathais, Schirmann and Weiss, *Bull. Soc. Chim. Fr.* 1972 (7) 2954; Schirmann and Weiss, *Tetrahedron Letters*, No. 7 635–636 (1972); Mathais, Schirmann, Tellier and Weiss, *Tetrahedron Letters*, No. 6, 529–530 (1972).

The oxidation reaction of Equation 1 can be accomplished with monopersulfuric acid (French application for patent Ser. No. 73/05.504 of Feb. 16, 1973), with a percarboxylic acid (pending U.S. application Ser. No. 290,507 filed Sept. 20, 1972, now French Pat. No. 2,155,134), or with a diacyl peroxide (U.S. Ser. No. 308,836 filed Nov. 22, 1972, corresponding to French applications Ser. Nos. 71/41867 and 72/08580, the former having matured into French Pat. No. 2,161,349, the latter being an application for Certificate of Addition thereto).

In strong contrast to the above-mentioned peroxide reagents, hydrogen peroxide by itself is not satisfactory. When it is attempted to oxidize ammonia and an aldehyde or ketone by simple reaction with hydrogen peroxide, many competing reactions take place simultaneously with little or no yield of azine. However, members of the present inventive entity have unexpectedly found that hydrogen peroxide can be used effectively to form azines selectively when certain adjuvant substances are also present, acting catalytically or as coreactants in a manner as yet not completely understood.

Thus, good yields of azines are obtained if the mixture of aldehyde or ketone with $H_2O_2$ and ammonia contains also a nitrile as coreactant (U.S. application for Pat. Ser. No. 152,413 filed June 11, 1971, corresponding to French applications for patent and certificate of addition respectively Ser. No. 70/46,994 filed Dec. 29, 1970 and Ser. No. 71/06,215 filed Feb. 24, 1971 which have since matured respectively into French Pat. Nos. 2,092,734 and 2,127,288).

Good yields of azines are also formed when the hydrogen peroxide, carbonyl compound and ammonia are reacted in the presence of coreacting amides or imides of carboxylic acids whose ionization constant is greater than $5 \times 10^{-5}$ (U.S. Ser. No. 341,057 filed Mar. 14, 1972, corresponding to French Pat. No. 2,177,215) or in the presence of cyanide compounds as co-reactants (French Pat. No. 2,176,244), in the presence of certain salts as catalyst (U.S. Ser. No. 267,921 filed June 30, 1972) or in the presence of certain esters as coreactants (U.S. Ser. No. 340,762 filed Mar. 13, 1973), or with a derivative of selenium as catalyst (Application for French patent Ser. No. 73/04,633 filed Feb. 9, 1973).

It has also been ascertained that when a system of hydrogen peroxide, ammonia, carbonyl compound (aldehyde or ketone) and one of the special adjuvants recited above contains also a primary and/or secondary amine (III), there takes place in addition to the reaction summarized in equation (1) above, the formation of a hydrazone (II) according to the following equation (2):

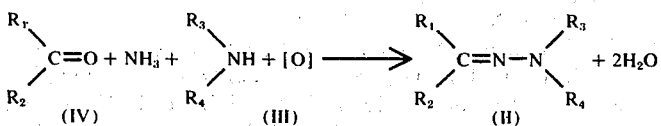

(2)

wherein the R groups can be such as those described further below herein in respect to the instant invention. See, for example, Application for U.S. patent Ser. No. 406467 filed Oct. 15, 1973, corresponding to application for French patent Ser. No. 72/36,505 filed Oct. 16, 1972; also the aforementioned French application Ser. No. 73/04,633 filed Feb. 9, 1973.

It is to be emphasized that when amides are used as coreactants according to the aforementioned applications Ser. No. 341,057 or 406,467, a limitation required in order to get good yields of azines or hydrazones respectively is that the carboxylic acid from which the amide is derived must be sufficiently strong to have a dissociation constant at least equal to about $5 \times 10^{-5}$, i.e. its pK must be less than about 4.3.

SUMMARY OF THE INVENTION

A means has now been found whereby amides of weaker acids can be used as effective coreactants enhancing the yields of azines (I) and/or hydrazones (II) produced by mixtures of an aldehyde or ketone with hydrogen peroxide and ammonia. It has unexpectedly been discovered that such can be accomplished by using as co-catalyst certain compounds having the general formula H—X—Y=Z wherein H is a hydrogen atom or its replacement by an alkali metal or ammonium; X and Z each is an atom of oxygen or nitrogen and Y is an atom of carbon, nitrogen, arsenic, antimony, phosphorus, sulfur, selenium or telluriam, the atoms of X, Y and Z carrying other substituents necessary to obey the rules of valence.

In particular, the present invention provides a method for preparing an azine or mixture of azines from one or more aldehydes or ketones which method comprises reacting said aldehydes or ketones with a mixture of ammonia and hydrogen peroxide in the presence of both (a) an amide of a carboxylic acid having a pK greater than about 4.3 and (b) as a co-catalyst, an acid or corresponding alkali-metal or ammonium salt of a phosphate, a phosphite, a mono- or di-($C_1$–$C_6$) alkyl phosphate ester, a polyphosphate, a pyrophosphate, an arsenate, a benzene or toluene sulfonate or phosphonate, a $C_1$–$C_6$ alkyl phosphonate, a sulfate or a sulfate ester with a $C_1$–$C_6$ alkyl alcohol, a bicarbonate, an antimonate or a stannate.

The present invention also provides a method for preparing a mixture of azines and hydrazones from one or more aldehydes or ketones which method comprises reacting said aldehydes or ketones with ammonia, hydrogen peroxide and a primary or secondary amine in the presence of both (a) an amide of carboxylic acid having a pK greater than about 4.3 and (b) as a co-catalyst, an acid or corresponding alkali-metal or ammonium salt of a phosphate, a phosphite, a mono- or di-($C_1$–$C_6$) alkyl phosphate ester, a polyphosphate, a pyrophosphate, an arsenate, a benzene or toluene sulfonate or phosphonate, a $C_1$–$C_6$ alkyl phosphonate, a sulfate or a sulfate ester with a $C_1$–$C_6$ alkyl alcohol, a bicarbonate, an anti-monate or a stannate.

DETAILED DESCRIPTION

In previous researches carried out by present applicants at the laboratories of the present assignee, it has been established that certain amides or imides of carboxylic acids can function as coreactant in the oxidation of ammonia and a carbonyl compound (i.e. an aldehyde or a ketone) by hydrogen peroxide, selectively forming an azine (I). As disclosed in the abovementioned U.S. Ser. No. 341,057, when the amide or imide is derived from a carboxylic acid whose ionization constant is greater than about $5 \times 10^{-5}$, the ammonium salt is formed along with the conversion of the aldehyde or ketone to azine, according to the overall equation

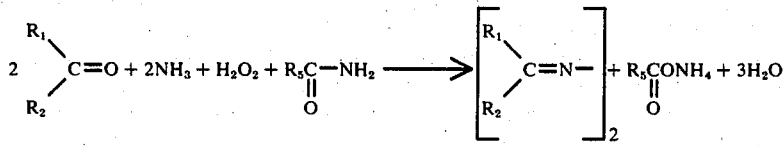

(3)

(wherein the R groups can be such as those described further below herein except that $R_5$ corresponds to any carboxy acids $R_5COOH$ in general).

However, the reaction represented by this equation (3) is extremely slow when the amide or imide is derived from a carboxylic acid whose ionization constant is less than about $5 \times 10^{-5}$. For example, when acetamide or urea is used as the amide, the reaction of equation (3) proceeds so slowly that the usual undesired reactions characteristic of systems without adjuvant take place instead. Thus the above-described earlier known reactions between ammonia and/or hydrogen peroxide with the aldehyde or ketone can dominate, or the simple basic decomposition of hydrogen peroxide can take place.

It has likewise been disclosed in abovementioned U.S. Ser. No. 406,467 that the presence of a primary or secondary amine along with ammonia, hydrogen peroxide, carbonyl compound and amide or imide, results in the production of a mixture of azine and hydrazone, again provided that the dissociation constant of the acid from which the amide or imide is derived, is greater than about $5 \times 10^{-5}$. When a corresponding mixture with an amide of a weaker acid is reacted, the amounts of azine and hydrazone produced are negligible because competitive undesired reactions take place more readily, including the basic decomposition of hydrogen peroxide.

Now the present invention teaches that rapid reactions leading to good yields of azines, or respectively of a mixture of azines and hydrazones, are effectuated when the mixture of carbonyl compound, ammonia, hydrogen peroxide, and optionally a primary or secondary amine, contains also both (a) an amide of a carboxylic acid having a dissociation constant less than about $5 \times 10^{-5}$ and (b) the co-catalyst of this invention as defined in greater detail above and below herein.

Researches undertaken by the applicants have established that both components (a) and (b) of this catalyst system can be recovered substantially unchanged at the termination of the process of this invention. In particular, the amide appears not appreciably hydrolyzed to the corresponding ammonium salt.

The mechanism whereby the amide and co-catalyst take part as co-reactants of the process to effect the unexpected selectivity is incompletely understood. It has been established as an empirical fact, however, that both the amide and the co-catalyst are surprisingly necessary to obtain rapid and selective formation of azine according to the equation

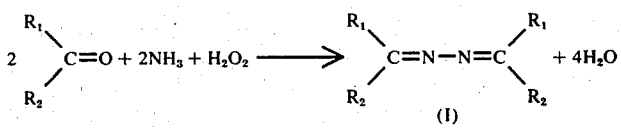

and, respectively, to obtain a mixture of azine and hydrazone when a primary or secondary amine is also present, by simultaneous reaction according to the equation

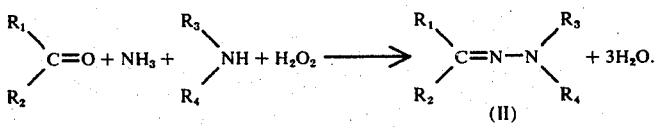

In the absence of either part of the two-component catalyst system of this invention, the selective formation of the desired azine product, or the desired mixture of azine and hydrazone products, is not achieved and satisfactory yields are not obtained.

The amides which function according to the present invention are derived from corresponding carboxylic acids which have an acid dissociation constant less than about $5 \times 10^{-5}$, i.e. acids which have a pK equal to or greater than 4.3 in aqueous solution at about 25°C. Said acid can exemplarily be carbonic acid or a monocarboxylic or a polycarboxylic $C_2-C_{21}$ fatty acid, straightchained, branched or cyclic; or a derivative of benzoic acid substituted on the benzene ring by hydroxy-, methoxy- or amino-groups to lower the dissociation constant. Thus the acid can be acetic, propionic, n-butyric, isobutyric, n-valeric, trimethylacetic, caproic, n-heptylic, cyclohexanecarboxylic or hexahydrobenzoic, caprylic, pelargonic, capric, undecanoic, lauric, n-tridecylic, myristic, n-pentadecylic, palmitic, margaric, stearic, nonadecanoic, arachidic or heneicosanoic acid. The polycarboxylic acids useful as parents of the amides in this invention are those whose first ionization constant is less than about $5 \times 10^{-5}$. Dicarboxylic acids whose first ionization constants are lower than $5 \times 10^{-5}$ include adipic, pimelic, suberic, azelaic and sebacic acids. Suitable aromatic carboxylic acids include p-hydroxybenzoic acid, anisic acid, gallic acid, anthranilic acid, m-aminobenzoic acid and p-aminobenzoic acid.

The preferred amides are acetamide and urea, both of which are economically advantageous as a result of their low cost, relatively low molecular weight and ready solubility in water.

Among the compounds serving as catalyst in the instant method and confronting to the general formula H—X—Y=Z defined above, there can be mentioned in particular, as non-limiting examples, the alkali-metal and ammonium salts of phosphates, phosphites, phosphonates, polyphosphates pyrophosphates, arsenates, bicarbonates, antimonates, stannates and sulfonates, as well as the esters of any of these with lower alkyl alcohols.

More particularly, the phosphorus compounds which can function as catalysts in this invention include the salts and/or esters of the mono- and polyphosphates generally and also the organo-phosphonates.

The term "mono- and polyphosphates generally" as used herein designates the phosphates having the formula $P_nO_{3n+1}M_{n+2}$ and those commonly called metaphosphates having the formula $(PO_3M)_n$ wherein M is hydrogen, ammonium, or an alkali metal and n is a whole number equal to or greater than 1. Thus the phosphate can be, illustratively, sodium orthophosphate or trisodium phosphate e.g. the dodecahydrate (TSP), disodium hydrogen orthophosphate, sodium dihydrogen orthophosphate, sodium pyrophosphate or dipolyphosphate (TSPP), disodium dihydrogen pyrophosphate $Na_2H_2P_2O_7$ commonly called sodium acid pyrophosphate, anhydrous or as hexahydrate, trisodium pyrophosphate, anhydrous or as heptahydrate, sodium trihydrogen pyrophosphate, pentasodium tripolyphosphate $Na_5P_3H_{10}$, (STPP), metaphosphoric acid $HPO_3$, sodium mono-metaphosphate $NaPO_3$, sodium trimetaphosphate $Na_3(PO_3)_3$, sodium tetrametaphosphate $Na_4(PO_3)_4$ or sodium hexametaphosphate or Graham's salt $(NaPO_3)_6$ or its technical grade mixtures known variously as calgon, quadrafos or micromet. The phosphate can be added directly as a sodium, potassium. lithium, ammonium, etc. salt of the respective phosphate, or the phosphate can be formed in situ in the reaction mixture by appropriate addition of exemplarily an alkali like sodium or lithium hydroxide and an acid like orthophosphoric or pyrophosphoric acid.

Corresponding examples of esters are mono and di substituted methyl, ethyl, propyl, isopropyl, n-butyl, isobutyl, sec butyl, tert butylphosphates, as well as the various amyl phosphates and hexyl phosphates. Thus, for example, the ester can be n-propyl dihydrogen phosphate or its alkali-metal or ammonium salts, di(isopropyl) hydrogen phosphate, n-butyl dihydrogen phosphate, di(n-butyl) hydrogen phosphate, sec-butyl dihydrogen phosphate n-amyl dihydrogen phosphate, n-hexyl dihydrogen phosphate, or cyclohexyl dihydrogen phosphate or any of the alkali-metal or ammonium salts of any of these esters.

The catalyst of the method of the instant invention can also be, exemplarily, sodium phosphite ($Na_2HPO_3$, $5H_2O$), a sodium salt of ethylphosphonic or butylphosphonic acid, lithium benzene phosphonate, disodium arsenate ($Na_2HAsO_4$), sodium selenate ($Na_2SeO_4$, $10H_2O$), sodium bicarbonate, ammonium p-toluene sulfonate, potassium acid pyroantimonate ($K_2H_2Sb_2O_7 \cdot H_2O$), sodium tellurate ($Na_2TeO_3$) or sodium stannate ($Na_2SnO_3 \cdot 3H_2O$).

The term "carbonyl compound" as used herein signifies an aldehyde or ketone having the formula

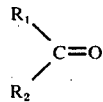

wherein $R_1$ and $R_2$ are identical or different and can be an atom of hydrogen or a ($C_1$–$C_{12}$) straight chain alkyl or a ($C_3$–$C_{12}$) branched alkyl or cycloalkyl or a ($C_6$–$C_{12}$) hydrocarbon radical having an aromatic ring such as benzene, naphthalene or pyridine; or $R_1$ and $R_2$ together can represent a $C_3$–$C_{11}$ alkylene radical, straight-chained or branched, wherein one of the carbons can be replaced by an oxygen atom. All these radicals can optionally be substituted, in place of hydrogen, by groups such as ethylene groups, chloro, bromo, iodo, fluoro, nitrile, nitro, hydroxy, alkoxy, carboxy, carbamyl or carbalkoxy groups.

Some examples of aldehydes which can be used advantageously as the carbonyl derivative (IV) in the process of this invention are formaldehyde, acetaldehyde, propionaldehyde, butyraldehyde, isobutyraldehyde, n-pentanal, caproic aldehyde, caprylic aldehyde, 2-ethylhexanal, trimethylacetaldehyde or pivalaldehyde, oenanthal, 3-Δ-tetrahydrobenzaldehyde, hexahydrobenzaldehyde, 5-norbornene-2-carboxaldehyde, tetrahydropyran-2-carboxaldehyde, benzaldehyde, the monochlorbenzaldehydes, p-nitrobenzaldehyde, anisaldehyde, β-chloropropionaldehyde, β-methoxypropionaldehyde and the like.

Some examples of ketones which can be likewise advantageously used are acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, isophorone, cycloheptanone, cyclooctanone, cyclodecanone, cyclododecanone and the like.

The primary and secondary amines $R_3$–$NH_2$ and

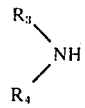

to prepare hydrazones according to this invention include those in which $R_3$ and $R_4$ are the same or different and are a ($C_1$–$C_{12}$) straight-chained alkyl or a $C_3$–$C_{12}$ branched or cycloalkyl or a $C_6$–$C_{12}$ hydrocarbon radical having a benzene, napthalene or pyridine ring; or $R_3$ and $R_4$ together can be a straight-chain or branched $C_3$–$C_{11}$ alkylene radical wherein one atom of carbon can be replaced by an oxygen atom. All these radicals can be substituted by atoms or groups such as atoms of fluorine, chlorine, bromine, iodine, hydroxy groups, alkoxy groups; or carboxy, carbamyl or carboxy-ester groups; or nitrile, nitro, sulfonic or sulfonamido groups. In the case of primary amines, $R_4$ is H.

Among the primary and secondary amines particularly useful in preparing hydrazones according to this invention there can be mentioned methylamine, dimethylamine, ethylamine, diethylamine, n-propylamine, isopropylamine, n-butylamine, di-(n-butyl) amine, isobutylamine, sec -butylamine, tert. butylamine, the amylamines, cyclohexylamine, di(cyclohexyl)amine, n-dodecylamine, 2-methoxyethylamine, morpholine, pyrrolidine, piperidine, betaaminopropionitrile, beta-aminopropionamide, aniline, the toluidines, mono - and di-chloroanilines or chlorotoluidines, the bromoanilines, the fluoroanilines, the nitroanilines, the dinitroanilines, the nitro and dinitro toluidines, orthoanisidine, meta-anisidine, para-anisidine, the trifluoromethylanilines, anthranilic acid, sulfanilic acid, diphenylamine, alpha-naphthylamine, beta-naphthylamine or the amino pyridines.

In carrying out the procedure of the instant invention the reactants are brought into contact in liquid medium, being mixed in any sequence whatsoever. For example, the reactants can be introduced separately or simultaneously into a reactor continuously or discontinuously; or the hydrogen peroxide can be introduced into a mixture containing the ammonia (and optionally the amine), the carbonyl compound (aldehyde or ketone) and the catalyst; or the ammonia or an ammoniacal solution can be added to a mixture containing the hydrogen peroxide, the aldehyde or ketone, the amide and the catalyst; or the amide can be added to a mixture containing the ammonia, hydrogen peroxide, aldehyde or ketone, catalyst and/or the corresponding aminoperoxides; or a preliminary mixture can be made of hydrogen peroxide and the aldehyde or ketone to obtain a mixture containing one or several known peroxide compounds of aldehyde or ketone and this mixture can be made to react with the ammonia, amide and catalyst; or other sequences of addition are also possible.

It can be advantageous to use a solvent or mixture of solvents to maintain a homogenous reaction medium or to attain at least a partial solubilization of the reactants. The preferred solvents are water and saturated $C_1$–$C_6$ alcohols, for example methanol, ethanol, n-propanol, isopropanol, n-butanol, secondary butanol, tertiary butanol, isobutanol, the amyl alcohols, and the hexyl alcohols including cyclohexanol.

The reaction can be effectuated over a large range of temperature extending from about 0° to about 100°C.

and under a pressure about equal to or greater than atmospheric, ranging up to about 10 atmospheres. Higher pressures in this range are advantageous when reactants are volatile and are thus maintained dissolved in the reaction mixture under pressure.

The reactants can be used in stoichiometric quantity, according to the equation presented above, but relatively greater or smaller proportions of the several reactants can also be used. By way of illustration, about 0.2 to 5 mols of aldehyde or ketone and of ammonia can be used per mol of hydrogen peroxide, about 2 to 4 mols being preferable.

The carboxylic amide can be used in the ratio of about 0.1 to 10 mols per mol of hydrogen peroxide; preferably about 2 to 5 mols of amide per mol of $H_2O_2$ are used.

The catalyst is used in ratio of about 0.01% to 10% by weight of the reaction mixture, preferably about 0.1 to 1%.

The reactants can be used in their common commercial form. Thus, in particular, the hydrogen peroxide can be used in aqueous solution containing from about 30 to 90% by weight of $H_2O_2$; and ammonia can be added as anhydrous ammonia or as the usual aqueous solutions.

It can also be advantageous to add to the reaction medium one or more substances known as stabilizers for peroxide compounds or substances having a buffering effect on the pH of the medium, such as exemplarily citric acid, nitrilotriacetic acid, ethylenediaminetetraacetic acid and the like, or their alkali-metal or ammonium salts. The proportion of each of such adjuvants can for example, be from about 0.01 to 1% by weight of the total mixture.

After the reaction of this invention has taken place, the azines and hydrazones can be recovered from the reaction mixture by known means such as, exemplarily, by liquid-liquid extraction, by fractional distillation, or by a combination of these two procedures.

The azines (I) and hydrazones (II) whose production constitutes the prime objective of the present invention are useful synthetic agents, especially in that they can be hydrolyzed by known methods to yield corresponding hydrazines or their salts with liberation of the aldehyde or ketone which can be recycled.

This invention will be further illustrated by description in connection with the following specific examples of the practice of it wherein, as also elsewhere herein, proportions are by weight unless stated otherwise. In all these examples, glass reactors of suitable dimensions were used, equipped with mechanical agitators and cooling means.

EXAMPLE 1

A reactor is charged with 69.6 grams of acetone (1.2 mol), 118 grams of acetamide (2 mols), 10 grams of the disodium salt of ethylenediaminetetraacetic acid (EDTA), 198 grams of water, and 0.286 grams of dilithium phosphate. Into this mixture there are dissolved 13.6 grams of ammonia (0.8 mol). The mixture is heated to 56°C and over a period of 30 minutes there is added 29.6 grams of a 70% by weight aqueous solution of hydrogen peroxide (0.6 mol). The mixture is then maintained at 56°C for 6 hours while passing a light current of gaseous ammonia at a rate of about 0.3 mol per hour. The quantity of acetone-azine formed in the reaction mixture, as determined by chemical means and by gas chromatography, is found to be 44.8 grams (0.4 mol) corresponding to a yield of 66.6% based on the hydrogen peroxide used.

EXAMPLE 2

Proceeding in a manner similar to that of Example 1, a reactor of suitable volume is charged with 34.8 grams of acetone (0.6 mol), 59 grams of acetamide (1 mol), 3 grams of the disodium salt of ethylenediaminetetraacetic acid (EDTA), 58.9 grams of water and 0.442 grams of monosodium carbonate. In this medium there is dissolved 6.8 grams of gaseous ammonia (0.4 mol). This mixture is then heated to 56°C and 15 grams of a 68% by weight aqueous solution of hydrogen peroxide (0.3 mol) is introduced over a period of 30 minutes. The temperature of the mixture is maintained at 56°C over a period of 5 hours while a current of gaseous ammonia is continuously passed at the rate of about 0.3 mol per hour. Analysis then shows that 18.6 grams of acetoneazine (0.167 mols) has been formed, corresponding to a yield of 55.6% based on the hydrogen peroxide used.

EXAMPLE 3

The procedure of Example 2 is followed except that the acetamide is replaced by 73 grams (1 mol) of propionamide, the amount of water is 91.4 grams and 0.19 grams of dilithium phosphate is added in place of the monosodium carbonate. All the other reactants are added in the same amounts and the reaction is carried out at the same temperature, 56°C. At the end of six hours, analysis shows 18.4 grams (0.165 mols) of acetone-azine, corresponding to a yield of 55% based on the hydrogen peroxide introduced.

EXAMPLE 4

Proceeding under conditions closely like those of Example 2, 43.2 grams (0.6 mol) of butanone-2 is used in place of the acetone, the amount of water is 48.5 grams and 0.119 grams of disodium phosphate is used instead of the monosodium carbonate. After 10.6 grams (0.625 mols) of ammonia is dissolved therein, the mixture is heated to 50°C and maintained at that temperature for 8 hours and 15 minutes, during the course of which a current of gaseous ammonia is passed through the mixture. At the end of this period, analysis shows 32.8 grams (0.234 mol) of butanone-2-azine in the reaction mixture. This corresponds to a yield of 78% based on the hydrogen peroxide used.

EXAMPLE 5

With conditions otherwise the same as in Example 3, 59 grams of acetamide (1 mol) and 59 grams of cyclohexanone (0.6 mol) are used. After 8 hours of reaction, analysis shows that the cyclohexanone-azine formed is 24.2 grams (0.126 mols) corresponding to a yield of 42% based on the hydrogen peroxide used.

EXAMPLE 6

The procedure of Example 3 is followed. A reactor is charged with 59 grams of acetamide (1 mol), 38 grams of acetone (0.65 mol) and 1 gram of an equimolecular mixture of mono- and di-isopropyl phosphates is used in place of the lithium phosphate. All the other reactants are identical as in Example 3. The reaction mixture is brought to 50°C and kept there for 7 hours 30 minutes, during which time a current of gaseous ammonia is bubbled through the mixture. At the end of this time the acetone-azine formed is found by analysis to be 16 grams (0.143 mol) which corresponds to a yield of 47.6% based on the hydrogen peroxide.

EXAMPLE 7

Working under the same conditions as in the preceding example, one replaces the mixture of isopropyl phosphates with one gram of a mixture of mono- and di-butyl phosphates. After 6 hours 30 minutes of reaction, analysis shows that 15.1 grams (0.135 mol) of acetone-azine are formed, corresponding to a 45% yield based on the hydrogen peroxide.

EXAMPLE 8

The procedure of Example 6 is followed with all materials being the same except that the catalyst used is 0.2 grams of paratoluene sulfonic acid. After a reaction duration of 7 hours 30 minutes, there is obtained 16.5 grams (0.147 mol) of acetone-azine, corresponding to a yield of 49% based on hydrogen peroxide.

EXAMPLE 9

A reactor is charged with 18 grams urea (0.3 mol), 35.8 grams acetone (0.6 mol), 142.3 grams water, 29 grams disodium arsenate, and 2 grams of the disodium salt of ethylene diaminetetraacetic acid (EDTA). Into this mixture there is dissolved 6.8 grams (0.4 mol) of ammonia. The mixture is then brought to a temperature of 58°C, 14.6 grams of a 70% by weight aqueous solution of hydrogen peroxide (0.3 mol) is introduced over a period of 15 minutes. The temperature is maintained at 58°C for 6 hours, during the course of which a current of gaseous ammonia is passed through the mixture at a rate of about 0.9 mols per hour. At the end of this reaction time, there is obtained 7.3 grams (0.065 mol) of acetone-azine, corresponding to a 21.6% yield based on hydrogen peroxide.

EXAMPLE 10

A reactor of suitable capacity is charged with 44.3 grams acetamide (0.75 mol), 26.1 grams acetone (0.45 mol), 20 grams water, 0.030 grams disodium phosphate, 41.9 grams aniline (0.45 mol), 1.5 grams of the disodium salt of ethylenediaminetetraacetic acid (EDTA) and 50 grams of methanol. Into this mixture 5.5 grams of gaseous ammonia (0.32 mol) is dissolved. Then the temperature is brought to 50°C and within 15 minutes 11.1 grams are added of 69% by weight aqueous solution of hydrogen peroxide (0.255 mol). The temperature of the mixture is maintained at 50°C over a period of 8 hours during the course of which a current of gaseous ammonia is passed through at the rate of about 0.1 mol per hour. At the end of this period it is found by chemical analysis and by gas chromatography that acetone-azine and acetone phenyl hydrazone are present in the medium. The amount of acetone-azine formed is 8.6 grams (0.077 mol) and the acetone phenyl hydrazone is 2.8 grams (0.019 mol) which corresponds to a yield of 42.7% based on the hydrogen peroxide used.

We claim:

1. A method for preparing an azine or a mixture of azines which comprises reacting (i) at least one carbonyl compound having the formula

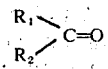

wherein $R_1$ and $R_2$, which can be identical or different, are each an atom of hydrogen or a ($C_1$–$C_{12}$) straight chain alkyl radical, a ($C_3$–$C_{12}$) branched alkyl or cycloalkyl radical, a phenyl radical, a naphthyl radical, or a pyridine radical, or $R_1$ and $R_2$ together represent a $C_3$–$C_{11}$ alkylene radical, straight-chained or branched, wherein one of the carbons may be replaced by an oxygen atom, the aforementioned radicals being unsubstituted or substituted with one or more halogen atoms or nitrile, nitro, hydroxy, alkoxy, carboxy, carbamyl or carbalkoxy groups, with (ii) a mixture of ammonia and hydrogen peroxide in the presence of (iii) both (a) an amide of a carboxylic acid having a pK equal to or greater than 4.3 or of a polycarboxylic acid having a first ionization constant equal to or greater than 4.3 and (b) a co-catalyst selected from the acids and the alkalimetal and ammonium salts of a phosphate, a phosphite, a mono- or di- ($C_1$–$C_6$) alkyl phosphate ester, a polyphosphate, a pyrophosphate, an arsenate, a benzene or toluene sulfonate or phosphonate, a ($C_1$–$C_6$) alkyl sulfate ester, a bicarbonate, an antimonate or a stannate.

2. The method of claim 1 wherein the carbonyl compound is selected from formaldehyde, acetaldehyde, propionaldehyde, butyraldehyde, isobutyraldehyde, n-pentanal, caproic aldehyde, caprylic aldehyde, 2-ethylhexanal, trimethylacetaldehyde, oenanthol, 3-Δ-tetrahydrobenzaldehyde, hexahydrobenzaldehyde, 5-norbornene-2-carboxaldehyde, tetrahydropyran-2-carboxaldehyde, anisaldehyde, β-chloropropionaldehyde, β-methoxypropionaldehyde, acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, isophorone, cycloheptanone, cycloocotanone, cyclodecanone, cyclododecanone and mixtures thereof.

3. The method of claim 1 wherein the amide is the amide of a carbonic acid or a monocarboxylic or polycarboxylic ($C_2$–$C_{21}$) linear, branched or cyclic fatty acid or a benzoic acid substituted with one or more hydroxy, methoxy, or amino groups.

4. The method of claim 3 wherein the amide is the amide of acetic, propionic, n-butyric, isobutyric, n-valeric, trimethylacetic, caproic, n-heptylic, hexahydrobenzoic, caprylic, pelargonic, capric, undecanoic, lauric, n-tridecyclic, myristic, n-pentadecyclic, palmitic, margaric, stearic, nonadecanoic, arachidic, heneicosanoic, adipic, pimelic, suberic, azelaic, sebacic, p-hydroxybenzoic, anisic, gallic, anthranilic, m-aminobenzoic or p-aminobenzoic acid.

5. The method of claim 4 wherein the amide is acetamide or urea.

6. The method of claim 1 wherein the co-catalyst is a salt or lower alkyl ester of the organophosphonates or of a phosphate having the formula $P_nO_{3n+1}M_{n+2}$ or $(PO_3M)_n$ wherein M is hydrogen, ammonium or an alkali metal and n is a whole number equal to or greater than 1.

7. The method of claim 6 wherein the co-catalyst is sodium orthophosphate, trisodium phosphate (TSP), disodium hydrogen orthophosphate, sodium dihydrogen orthophosphate, sodium pyrophosphate or dipolyphosphate (TSPP), disodium dihydrogen pyrophosphate $Na_2H_2P_2O_7$, anhydrous or as hexahydrate, trisodium pyrophosphate, anhydrous or as heptahydrate, sodium trihydrogen pyrophosphate, pentasodium tripolyphosphate $Na_5P_3H_{10}$, (STPP), metaphosphoric acid $HPO_3$, sodium mono-metaphosphate $NaPO_3$, sodium trimetaphosphate $Na_3(PO_3)_3$, sodium tetrametaphosphate $Na_4(PO_3)_4$ or sodium hexametaphosphate $(NaPO_3)_6$, or its sodium phosphite $(NaHPO_3 . 5H_2O)$, a sodium salt of ethylphosphonic or butylphosphonic acid, lithium benzene phosphonate, disodium arsenate $(Na_2HAsO_4)$, sodium selenate $(Na_2SeO_4 . 10H_2O)$, sodium bicarbonate, ammonium p-toluene sulfonate, potassium acid pyrontimonate $(K_2H_2Sb_2O_7 . H_2O)$, sodium tellurate $(Na_2TeO_3)$ or sodium stannate $(Na_2SnO_3 . 3H_2O)$.

8. The method of claim 1 wherein the alkyl phosphate ester is n-propyl dihydrogen phosphate, di(isopropyl) hydrogen phosphate, n-butyl dihydrogen phosphate, di(n-butyl) hydrogen phosphate, sec-butyl dihydrogen phosphate, n-amyl dihydrogen phosphate, n-hexyl dihydrogen phosphate or cyclohexyl dihydrogen phosphate or any of the alkali-metal or ammonium salts thereof.

9. The method of claim 1 wherein the reaction takes place in a solvent selected from water or a $(C_1-C_6)$ saturated alcohol.

10. A method for preparing an azine or a mixture of azines which comprises reacting:
    a. hydrogen peroxide;
    b. ammonia;
    c. a carbonyl compound selected from formaldehyde, acetaldehyde, propionaldehyde, butyraldehyde, isobutyraldehyde, n-pentanal, caproic aldehyde, caprylic aldehyde, 2-ethylhexanal, trimethylacetaldehyde, oenanthal, 3-Δ-tetrahydrobenzaldehyde, hexahydrobenzaldehyde, 5-norbornene-2-carboxaldehyde, tetrahydropyran-2-carboxaldehyde, benzaldehyde, the monochlorbenzaldehydes, p-nitrobenzaldehyde, anisaldehyde, β-chloropropionaldehyde, β-methoxypropionaldehyde, acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, isophorone, cycloheptanone, cyclooctanone, cyclodecanone and cyclododecanone, and mixtures thereof;
    d. an amide of acetic, propionic, n-butyric, isobutyric, n-valeric, trimethylacetic, caproic, n-heptylic, hexahydrobenzoic, caprylic, pelargonic, capric, undecanoic, lauric, n-tridecyclic, myristic, n-pentadecyclic, palmitic, margaric, stearic, nonadecanoic, arachidic, heneicosanoic, adipic, pimelic, suberic, azelaic, sebacic, p-hydroxybenzoic, anisic acid, gallic acid, anthranilic acid, m-aminobenzoic or p-aminobenzoic acid; and
    e. a co-catalyst selected from sodium orthophosphate, trisodium phosphate (TSP), disodium hydrogen orthophosphate, sodium dihydrogen orthophosphate, sodium pyrophosphate or dipolyphosphate (TSPP), disodium dihydrogen pyrophosphate $Na_2H_2P_2O_7$, anhydrous or as hexahydrate, trisodium pyrophosphate, anhydrous or as heptahydrate, sodium trihydrogen pyrophosphate, pentasodium tripolyphosphate $Na_5P_3H_{10}$, (STPP), metaphosphoric acid $HPO_3$, sodium mono-metaphosphate $NaPO_3$, sodium trimetaphosphate $Na_3(PO_3)_3$, sodium tetrametaphosphate $Na_4(PO_3)_4$ or sodium hexametaphosphate $(NaPO_3)_6$, sodium phosphite $(Na_2HPO_3, 5H_2O)$, a sodium salt of ethylphosphonic or butylphosphonic acid, lithium benzene phosphonate, disodium arsenate $(Na_2HAsO_4)$, sodium selenate $(Na_2SeO_4, 10H_2O)$, sodium bicarbonate, ammonium p-toluene sulfonate, potassium acid pyroantimonate $(K_2H_2Sb_2O_7.H_2O)$, sodium tellurate $(Na_2TeO_3)$ and sodium stannate $(Na_2SnO_3 . 3H_2O)$; and from n-propyl dihydrogen phosphate, di(isopropyl) hydrogen phosphate, n-butyl dihydrogen phosphate, di (n-butyl) hydrogen phosphate, sec-butyl dihydrogen phosphate, n-amyl dihydrogen phosphate, n-hexyl dihydrogen phosphate and cylcohexyl dihydrogen phosphate and the alkali-metal and ammonium salts thereof.

11. A method for preparing a mixture of at least one azine and at least one hydrazone which comprises reacting (i) at least one carbonyl compound having the formula

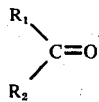

wherein $R_1$ and $R_2$, which can be identical or different are each an atom of hydrogen or a $(C_1-C_{12})$ straight chain alkyl radical, a $(C_3-C_{12})$ branched alkyl or cycloalkyl radical, a phenyl radical, a naphthyl radical, or a pyridine radical, or $R_1$ and $R_2$ together represent a $C_3-C_{11}$ alkylene radical, straight-chained or branched, wherein one of the carbons may be replaced by an oxygen atom, the aforementioned radicals being unsubstituted or substituted with one or more halogen atoms or nitrile, nitro, hydroxy, alkoxy, carboxy, carbamyl or carbalkoxy groups, with (ii) a mixture of ammonia, hydrogen peroxide and at least one amine of formula

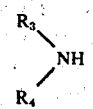

wherein $R_3$ and $R_4$, which can be identical or different, are each a $(C_1-C_{12})$ straight-chained alkyl radical, a $(C_3-C_{12})$ branched alkyl or cycloalkyl radical, a phenyl radical, a naphthyl radical, or a pyridine radical, or $R_3$ and $R_4$ together can be a straight-chained or branched $(C_3-C_{11})$ alkylene radical wherein one of the carbon atoms may be replaced by an oxygen atom, the aforementioned radicals being unsubstituted or substituted by one or more halogen atoms or hydroxy, alkoxy, carboxyl, carbamyl, nitrile, nitro, sulfonic or sulfonamide groups, or $R_4$ can be hydrogen, in the presence of (iii) both (a) an amide of a carboxylic acid having a pK equal to or greater than 4.3 or of a polycarboxylic acid having a first ionization constant equal to or greater than 4.3 and (b) a co-catalyst selected from the acids and the alkali-metal and ammonium salts of a phosphate, a phosphite, a mono- or di- $(C_1-C_6)$ alkyl phosphate ester, a polyphosphate, a pyrophosphate, an arsenate, a benzene or toluene sulfonate or phosphonate, a $(C_1-C_6)$ alkyl phosphonate, a sulfate, a $(C_1-C_6)$ alkyl sulfate ester, a bicarbonate, an antimonate or a stannate.

12. The method of claim 11, wherein the carbonyl compound is selected from formaldehyde, acetaldehyde, propionaldehyde, butyraldehyde, isobutyraldehyde, n-pentanal, caproic aldehyde, caprylic aldehyde, 2-ethylhexanal, trimethylacetaldehyde, oenanthol, 3-Δ-tetrahydrobenzaldehyde, hexahydrobenzaldehyde, 5-norbornene-2-carboxaldehyde, tetrahydropyran-2-carboxaldehyde, anisaldehyde, β-chloropropionaldehyde, β-methoxypropionaldehyde, acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, isophorone, cycloheptanone, cyloocotanone, cyclodecanone, cyclododecanone and mixtures thereof.

13. The method of claim 11 wherein the amide is the amide of a carbonic acid or a monocarboxylic or polycarboxylic $C_2$–$C_{21}$ linear, branched or cyclic fatty acid or a benzoic acid substituted with one or more hydroxy, methoxy, or amino groups.

14. The method of claim 13 wherein the amide is the amide of acetic, propionic, n-butyric, isobutyric, n-valeric, trimethylacetic, caproic, n-heptylic, hexahydrobenzoic caprylic, pelargonic, capric, undecanoic, lauric, n-tridecyclic, myristic, n-pentadecyclic, palmitic, margaric, stearic, nonadecanoic, arachidic, heneicosanoic, adipic, pimelic, suberic, azelaic, sebacic, p-hydroxybenzoic, anisic, gallic, anthranilic, m-aminobenzoic or p-aminobenzoic acid.

15. The method of claim 14 wherein the amide is acetamide or urea.

16. The method of claim 11 wherein the co-catalyst is a salt or lower alkyl ester of the organophosphonates or of a phosphate having the formula $P_nO_{3n+1}M_n+_2$ or $(PO_3M)_n$ wherein M is n+ hydrogen, ammonium or an alkali metal and n is a whole number equal to or greater than 1.

17. The method of claim 16 wherein the co-catalyst is sodium orthophosphate, trisodium phosphate (TSP), disodium hydrogen orthophosphate, sodium dihydrogen orthophosphate, sodium pyrophosphate or dipolyphosphate (TSPP), disodium dihydrogen pyrophosphate $Na_2H_2P_2O_7$, anhydrous or as hexahydrate, trisodium pyrophosphate, anhydrous or as heptahydrate, sodium trihydrogen pyrophosphate, pentasodium tripolyphosphate $Na_5P_3H_{10}$, (STPP), metaphosphoric acid $HPO_3$, sodium mono-metaphosphate $NaPO_3$, sodium trimetaphosphate $Na_3(PO_3)_3$, sodium tetrametaphosphate $Na_4(PO_3)_4$ or sodium hexametaphosphate $(NaPO_3)_6$, or its sodium phosphite $(Na_2HPO_3 . 5H_2O)$, a sodium salt of ethylphosphonic or butylphosphonic acid, lithium benzene phosphonate, disodium arsenate $(NaHAsO_4)$, sodium selenate $(NaSeO_4 . 10H_2O)$, sodium bicarbonate, ammonium p-toluene sulfonate, potassium acid pyroantimonate $(K_2H_2Sb_2O_7.H_2O)$, sodium tellurate $(Na_2TeO_3)$ or sodium stannate $(Na_2SnO_3 . 3H_2O)$.

18. The method of claim 11 wherein the alkyl phosphate ester is n-propyl dihydrogen phosphate, di(isopropyl) hydrogen phosphate, n-butyl dihydrogen phosphate, di(n-butyl) hydrogen phosphate, sec-butyl dihydrogen phosphate, n-amyl dihydrogen phosphate, n-hexyl dihydrogen phosphate, or cyclohexyl dihydrogen phosphate or any of the alkali-metal or ammonium salts thereof.

19. The method of claim 11 wherein the amine is selected from methylamine, dimethylamine, ethylamine, diethylamine, n-propylamine, isopropylamine, n-butylamine, di-(n-butyl) amine, isobutylamine, sec-butylamine, tert-butylamine, the amylamines, cylcohexylamine, di(cyclohexyl)amine, n-dodecylamine, 2-methoxyethylamine, morpholine, pyrrolidine, piperidine, beta-aminopropionitrile, beta-aminopropionamide, aniline, the toluidines, mono- and di-chloroanilines or chlorotoluidines, the bromoanilines, the fluoroanilines, the nitroanilines, the dinitroanilines, the nitro and dinitro toluidines, ortho-anisidine, meta-anisidine, para-anisidine, the trifluoromethylanilines, anthranilic acid, sulfanilic acid, diphenylamine, alpha-naphthylamine, beta-naphthylamine and the amino pyridines.

20. The method of claim 11 wherein the reaction takes place in a solvent selected from water or a $C_1$–$C_6$ saturated alcohol.

21. A method for preparing a mixture of at least one azine and at least one hydrazone which comprises reacting:
a. hydrogen peroxide; b. ammonia; c. a carbonyl compound selected from formaldehyde, acetaldehyde, propionaldehyde, butyraldehyde, isobutyraldehyde, n-pentanal, caproic aldehyde, caprylic aldehyde, 2-ethylhexanal, trimethylacetaldehyde or pivalaldehyde, oenanthol, 3-Δ-tetrahydrobenzaldehyde, hexahydrobenzaldehyde, 5-norbornene-2-carboxaldehyde, tetrahydropyran-2-carboxaldehyde, benzaldehyde, the monochlorbenzaldehydes, p-nitrobenzaldehyde, anisaldehyde, β-chloropropionaldehyde, β-methoxypropionaldehyde, acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone 2-methylcyclohexanone, 3-methylcyclohexanone, 4-methylcyclohexanone, 2,4-dimethylcyclohexanone, 3,3,5-trimethylcyclohexanone, isophorone, cycloheptanone, cyclooctanone, cyclodecanone and cyclododecanone, and mixtures thereof;
d. one or more amines selected from methylamine, dimethylamine, ethylamine, diethylamine, n-propylamine, isopropylamine, n-butylamine, di-(n-butyl)amine, isobutylamine, sec-butylamine, tert-butylamine, the amylamines, cyclohexylamine, di(cyclohexyl)amine, n-dodecyclamine, 2-methoxyethylamine, morpholine, pyrrolidine, piperidine, beta-aminopropionitrile, beta-aminopropionamide, aniline, the toluidines, mono- and di-chloroanilines or chlorotoluidines, the bromoanilines, the fluoroanilines, the nitroanilines, the dinitroanilines, the nitro and dinitro toluidines, ortho-anisidine, meta-anisidine, para-anisidine, the trifluoromethylanilines, anthranilic acid, sulfanilic acid, diphenylamine, alpha-naphthylamine, beta-naphthylamine and the amino pyridines, and mixtures thereof;
e. an amide of acetic, propionic, n-butyric, isobutyric, n-valeric, trimethylacetic, caproic, n-heptylic, cyclohexanecarboxylic or hexahydrobenzoic, caprylic, pelargonic, capric, undecanoic, lauric, n-tridecylic, myristic, n-pentadecylic, palmitic, margaric, stearic, nonadecanoic, arachidic, heneicosanoic, adipic, pimelic, suberic, azelaic, sebacic, p-hydroxybenzoic, anisic, gallic, anthranilic, m-aminobenzoic or p-aminobenzoic acid; and f. a phosphate selected from sodium orthophosphate or trisodium phosphate (TSP), disodium hydrogen orthophosphate, sodium dihydrogen orthophosphate, sodium pyrophosphate or dipolyphosphate (TSPP), disodium dihydrogen pyrophosphate $Na_2H_2P_2O_7$, anhydrous or as hexahydrate, trisodium pyrophosphate, anhydrous or as heptahydrate, sodium trihydrogen pyrophosphate, pentasodium tripolyphosphate $Na_5P_3H_{10}$, (STPP), metaphosphoric acid $HPO_3$, sodium mono-metaphosphate $NaPO_3$, sodium trimetaphosphate $Na_3(PO_3)_3$, sodium tetrametaphosphate $Na_4(PO_3)_4$ or sodium hexametaphosphate $(NaPO_3)_6$, a sodium phosphite ($Na_2HPO_3$, $5H_2O$), a sodium salt of ethylphosphonic or butylphosphonic acid, lithium benzene phosphonate, disodium arsenate ($Na_2HAsO_4$), sodium selenate ($Na_2SeO_4$, $10H_2O$), sodium bicarconate, ammonium p-toluene sulfonate, potassium acid pyroantimonate ($K_2H_2Sb_2O_7 \cdot H_2O$), sodium tellurate ($Na_2TeO_3$) and sodium stannate ($Na_2SnO_3 \cdot 3H_2O$), n-propyl dihydrogen phosphate, di(isopropyl) hydrogen phosphate, n-butyl dihydrogen phosphate, di(n-butyl hydrogen phosphate, sec-butyl dihydrogen phosphate, n-amyl dihydrogen phosphate, n-hexl dihydrogen phosphate and cyclohexyl dihydrogen phosphate and the alkali-metal and ammonium salts thereof.

* * * * *

UNITED STATES PATENT AND TRADEMARK OFFICE
CERTIFICATE OF CORRECTION

PATENT NO. : 3,972,878
DATED : August 3, 1976
INVENTOR(S) : Jean-Pierre Schirmann et al.

It is certified that error appears in the above-identified patent and that said Letters Patent are hereby corrected as shown below:

Foreign Application Priority Data "Feb. 8, 1974....74.4247" should be --Feb. 8, 1974....74 04247--

Column 15, line 40 "...wherein M is n + hydrogen" should be --...wherein M is hydrogen--

Signed and Sealed this

Sixteenth Day of November 1976

[SEAL]

Attest:

RUTH C. MASON
*Attesting Officer*

C. MARSHALL DANN
*Commissioner of Patents and Trademarks*